United States Patent
Efstathiou et al.

(10) Patent No.: US 6,193,980 B1
(45) Date of Patent: *Feb. 27, 2001

(54) REPLICATION DEFECTIVE HERPES SIMPLEX VIRUS COMPRISING HETEROLOGOUS INSERTS

(75) Inventors: Stacey Efstathiou; Robin H. Lachmann, both of Cambridge (GB)

(73) Assignee: Cambridge University Technical Services, Limited, Cambridge (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/875,225

(22) PCT Filed: Dec. 6, 1996

(86) PCT No.: PCT/GB96/03033

§ 371 Date: Sep. 17, 1997

§ 102(e) Date: Sep. 17, 1997

(87) PCT Pub. No.: WO97/20935

PCT Pub. Date: Jun. 12, 1997

(30) Foreign Application Priority Data

Dec. 6, 1995 (GB) .................................... 9524973

(51) Int. Cl.[7] .................... A61K 39/12; C12N 15/00; C12N 1/12

(52) U.S. Cl. ................... 424/199.1; 424/204.1; 424/229.1; 435/5; 435/235.1; 435/320.1; 435/173.3; 514/44

(58) Field of Search .................. 424/199.1, 204.1, 424/229.1; 435/5, 235.1, 320.1, 173.3, 172.3, 172.7; 514/44

(56) References Cited

FOREIGN PATENT DOCUMENTS

93/03143   2/1993   (WO).
94/24301   10/1994  (WO).

OTHER PUBLICATIONS

Efstathiou et al., "Herpes Virus–Based Vectors," *British Medical Bulletin*, 51:45–55 (1995).

Glorioso et al., "HSV as a Gene Transfer Vector for the Nervous System," *Molecular Biotechnology*, 4:8799 (1995).

Miyanohara et al., "Direct Gene Transfer to the Liver with Herpes Simplex Type 1 Vectors: Transient Production of Physiologically Relevant Levels of Circulating Factor IX," *The New Biologist*, 4(3):238–246 (1992).

Orkin et al, 1995, NIH Report in Resarch on Gene Theraphy, Dec. 7, 1995.*

Verma et al, Nature, vol. 389, pp. 239–242, Sep. 18, 1997.*

* cited by examiner

*Primary Examiner*—Ali R. Salimi
(74) *Attorney, Agent, or Firm*—Klarquist Sparkman Campbell Leigh & Whinston, LLP

(57) ABSTRACT

Constructs for the delivery of sequences of interest to cells include a herpes virus latency active promoter (LAP) of the latency associated transcript (LAT) region. An internal ribosome entry site (IRES) is located downstream of the LAP, with a nucleotide sequence of interest downstream of the IRES. Stable, long-term expression including export of mRNA to the cytoplasm and translation of the encoded polypeptide, is found in neuronal and non-neuronal cells.

9 Claims, 7 Drawing Sheets

Figure 1:
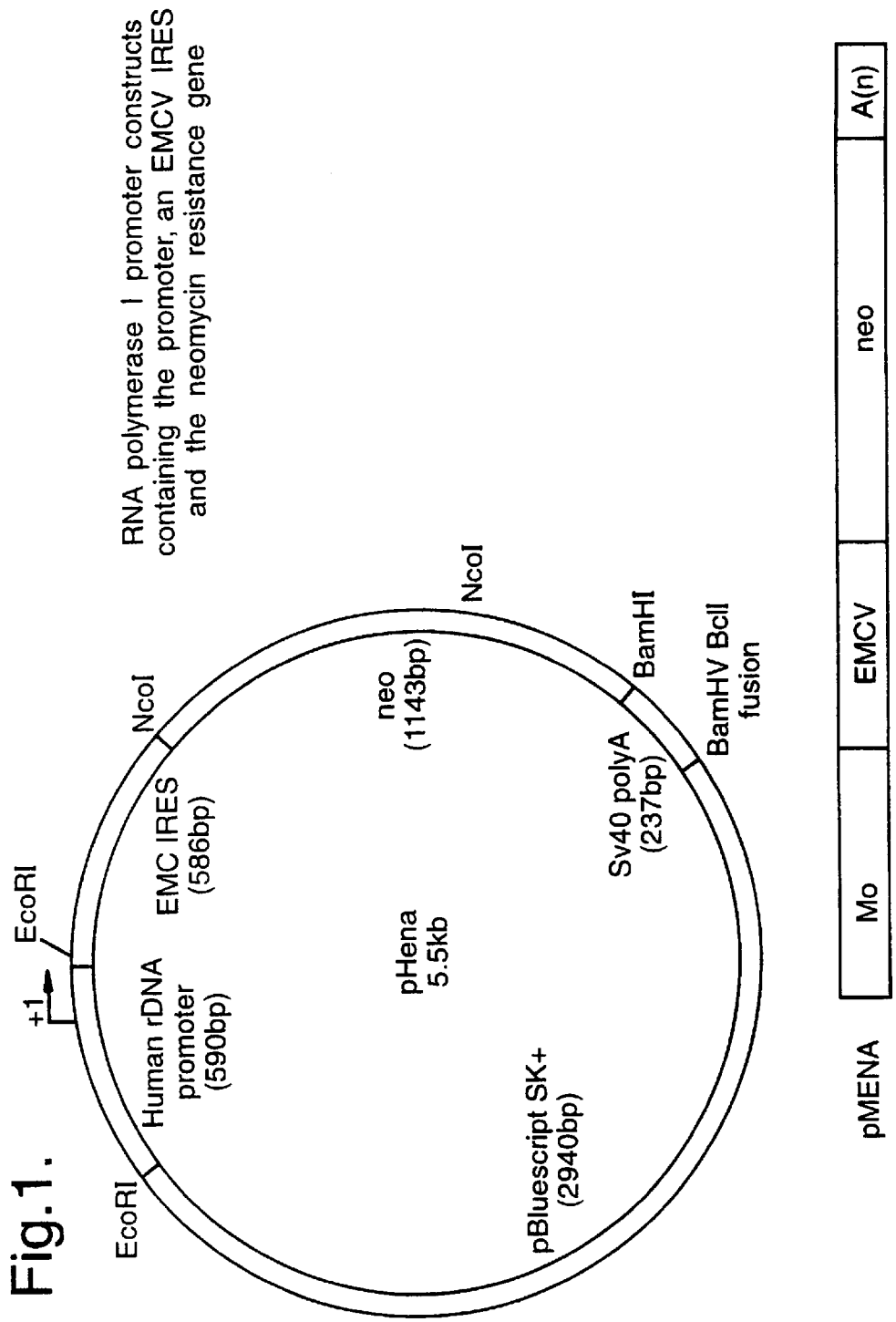

Fig.6a.
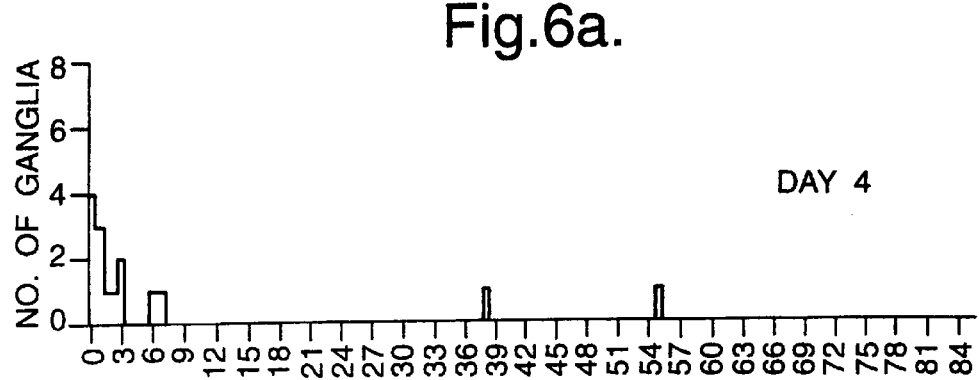
DAY 4
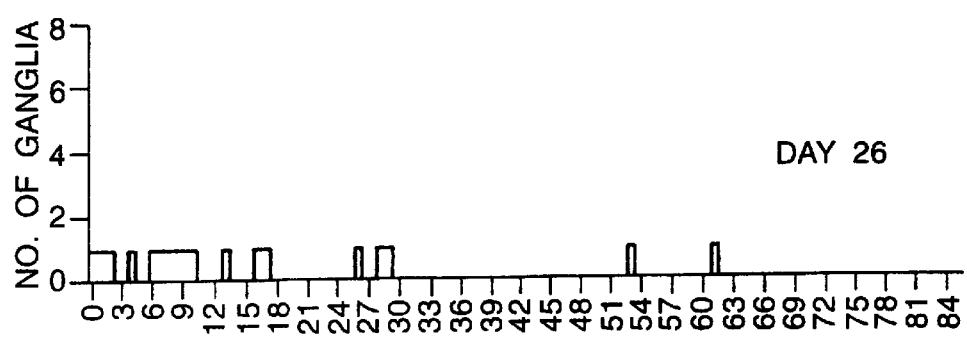
DAY 26
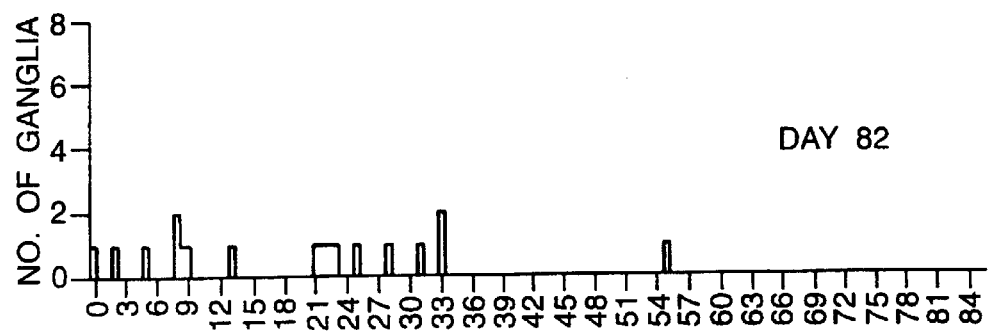
DAY 82
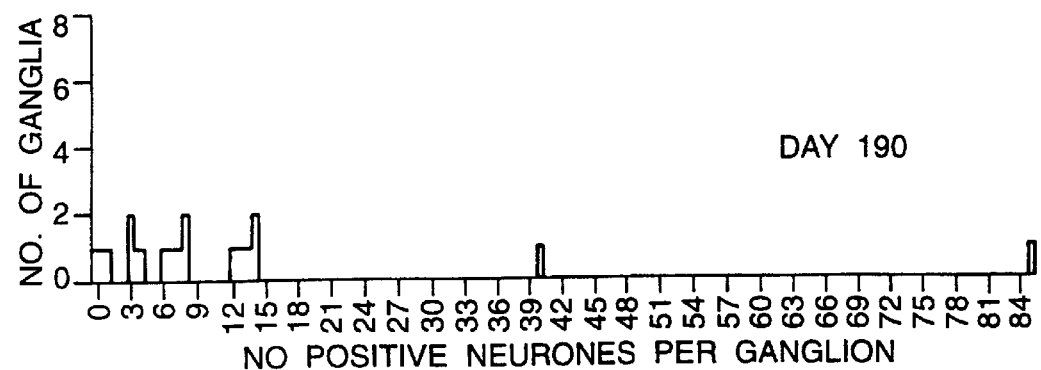
DAY 190
NO POSITIVE NEURONES PER GANGLION

Fig.6b.
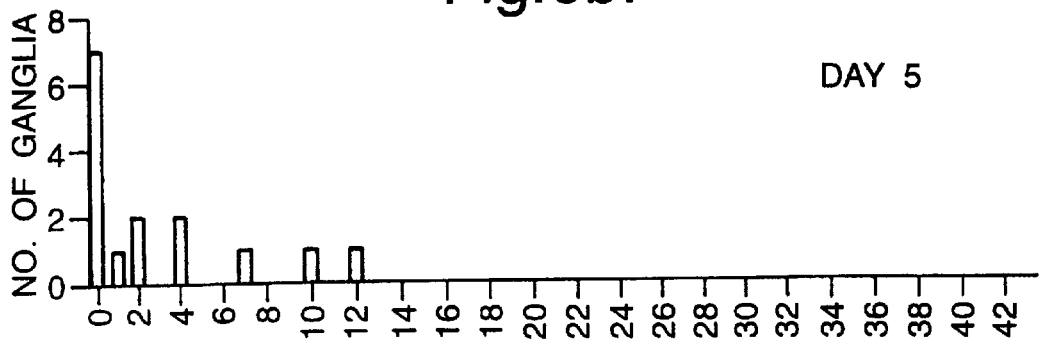
DAY 5
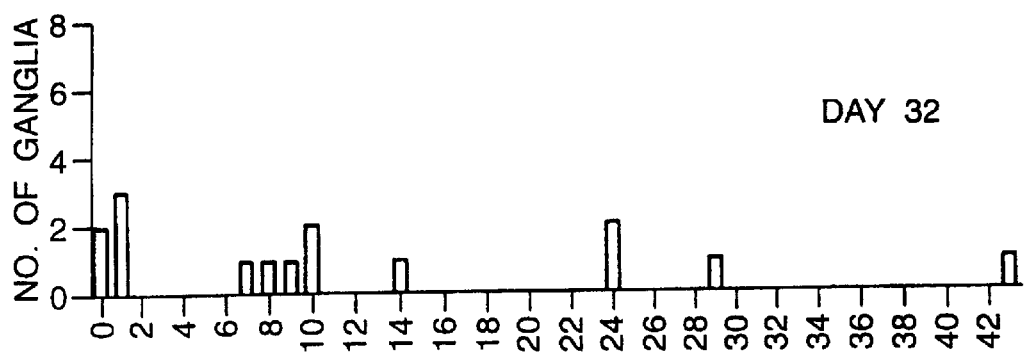
DAY 32
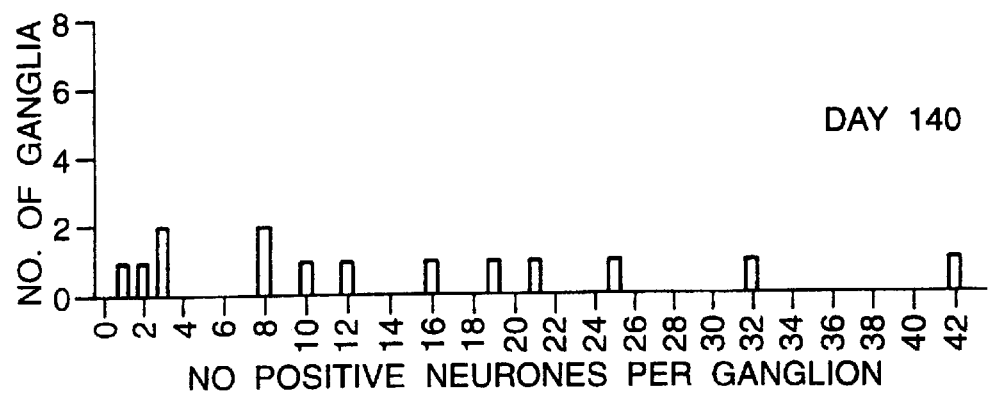
DAY 140
NO POSITIVE NEURONES PER GANGLION

REPLICATION DEFECTIVE HERPES SIMPLEX VIRUS COMPRISING HETEROLOGOUS INSERTS

The present invention relates to constructs for delivery of sequences of interest to cells of an individual, for instance using recombinant viruses. This can have a therapeutic aim: and examples of the constructs and cells containing them can be useful also, for example, in production of a polypeptide which can then be used as desired (e.g. as an immunogen). By employing a latency active promoter of a latency associated transcript (LAT) region of a herpes simplex virus, long-term, high-level expression of a reporter sequence can be achieved.

It is often desirable to deliver exogenous DNA to cells in order to provide a missing gene or to help correct abnormal cellular behaviour. The present invention is not generally concerned with any difficulties that may be associated with delivery of nucleic acid to cells.

Many viruses have evolved to deliver nucleic acid into the nucleus of the cell, where it can be expressed. Certain viruses have been genetically engineered to carry a gene to be delivered, and can deliver it to host cells such as those the virus normally infects. Gene delivery vectors have also been based on attenuated or genetically disabled virus.

A number of genetically engineered viruses have been used to deliver foreign genes to cells both in vitro and in vivo. For certain purposes it is desirable for the gene to be stably expressed, producing biologically active amounts of its product on a long term basis. This remains a problem in a number of contexts.

Herpes Simplex Virus (HSV) is a ubiquitous pathogen of man which is capable of acutely infecting many cell types, and can persist long term in the sensory neurons of the host's dorsal root ganglia. This state, described as viral latency, is characterised by the persistence of the viral genome in the nucleus of the neuron without any detectable production of viral proteins, or interference with normal cellular metabolism. HSV's ability to establish latency in neurons makes it an attractive-candidate as a gene delivery vector for the nervous system.

Though the virus does not produce any detectable protein product during latency, there is continuing RNA transcription. This latency associated transcription comes from a single region of the viral genome (the latency associated transcript or LAT region) and is driven by the latency active promoter (LAP). The TATA box and basal transcriptional regulatory sequences, which constitute the core LAT promoter, reside approximately 700 bp upstream of the 2 kb major LAT.

HSV-1 is considered a good candidate vector for CNS gene therapy because it is able to establish life-long latent infections in human sensory neurons. During latency, the viral genome appears to be maintained episomally, and hence there appears to be no danger of insertional mutagenesis or inactivation of host genes. Furthermore, there is no detectable production of viral proteins during latency, and no evidence that the latent state interferes with the normal metabolism of the host cell.

Viral gene expression during latency appears to be limited to 2 or 3 nuclear RNA species which accumulate to high levels in sensory neurons harbouring latent virus (the LATs) (3). These transcripts are driven by a complex promoter region (LAP) (4). A functional-LAT region is not essential for the establishment of latency, and viruses whose LAT region has been deleted can still establish latency (5), and in some cases, express LATs (6). In fact it seems that the LATs may be involved in reactivation, as LAT negative viruses do not reactivate efficiently (7). Latency can be established in the absence of any viral gene expression, and seems to be a default pathway for the virus when it enters a cell where productive infection is not possible.

Studies using diverse promoters to drive expression of a reporter gene (usually β-galactosidase) in animal models, have shown transient reporter gene expression, but that this is not long-lived. This has led to much work trying to define what elements of the LAT region and promoter (LAP) are involved in maintaining its long-term transcriptional activity. Further work has been done to try to utilise the LAP and other sequence elements in the LAT region to facilitate long-term expression of reporter genes.

A rabbit β-globin gene inserted downstream of the TATA box of the LAP made β-globin RNA during latent infection, but at lower levels than LAT in wild type infection (8). When the experiments were repeated using the endogenous LAT promoters to drive β-galactosidase or nerve growth factor genes, no RNA could be detected by in situ hybridisation (9).

The same group have since used a recombinant defective virus with a Moloney Murine Leukaemia Virus (MMLV) LTR, Lac Z construct inserted into ICP4, and a deletion of the 5' part of LAT, and demonstrated β-galactosidase expression in sensory ganglia (10). Gene expression was also assessed in motor neurons of the hypoglossal nucleus, where there was abundant transient expression. The results were taken to indicate that the MMLV LTR did not remain active during latency in motor neurons. When the MMLV LTR is moved away from the viral repeats (where it is near to endogenous LAT sequences) and inserted into the gC locus, it was not longer able to produce long-term gene expression. If the region upstream of the LAP is also inserted into the gC locus upstream of the LTR, this virus is capable of producing gene expression in sensory neurons. The LAT sequences did not have similar facilitating effects when inserted upstream of the murine metallothionein promoter (11).

Other groups have also used the LAT promoter in vectors. Wolfe et al used a recombinant virus with the β-glucoronidsase (GUSB) gene inserted into a LAT deletion downstream of the LAP in an attempt to correct the deficiency in GUSB deficient mice (12). A corneal infection route was used, and, although there was no phenotypic improvement in the condition of the mice, they were able to detect some GUSB positive cells as much as 18 weeks post inoculation. Miyanohara et al have used a variety of HSV-1 vectors to attempt to deliver genes to the liver of mice (13). Using a LAT promoter to drive HbsAg or canine factor IX, they saw low levels of protein in the serum for about 3 weeks after direct injection of the vector into the liver.

These studies suggest that the LAT promoter may be able to produce prolonged, albeit low level, expression of foreign genes in the CNS and even in non-neuronal cells.

Goins et al. *J. Virol.* 68: 2239–2252 (1994) and WO96/27672 postulated the presence of a second latency-active promoter, tested for by experiments involving transient gene expression, located in the HSV1 $U_L$ flanking repeats.

Specification WO 96/27672 (published later than the priority date claimed for the present application) (Glorioso & Fink) concerns the structure of a herpesvirus promoter for transcription of a non-herpes gene in a cell latently infected with a herpes virus, e.g. peripheral neurons and cranial nerve ganglia.

HSV-1 based vectors have also been constructed using lytic cycle HSV promoters (gC (14), IE110 (15)), strong non-specific promoters (CMV IE MMLV LTR) and neuron specific promoters (NSE (16)). On the whole, these studies show only transient gene expression in both peripheral and CNS neurons. As discussed above, the MMLV LTR can give long-term expression, but only when inserted close to LAT elements.

The present inventors now show experimentally that by inserting a reporter gene, preceded by an internal ribosomal entry site (to allow efficient translation), downstream of the LAP in the LAT region, a vector that gives stable, high level reporter gene expression during viral latency can be produced.

In initial attempts to construct HSV vectors which would give long-term gene expression the present inventors decided to use a murine RNA polymerase I (RNA pol I) promoter reporter gene construct inserted into the LAT region. RNA pol I is responsible for the transcription of ribosomal RNAs, and is active in all cell types. Native RNA pol I transcripts are not capped, and are not recognised by the translational apparatus of the cell, but, by inserting an internal ribosomal entry site (IRES) sequence immediately upstream of the reporter gene, it is possible to get efficient translation from such a transcript (17). By inserting this construct into the LAT region of HSV, which is known to be transcriptionally active during latency, the present inventors hoped to show RNA pol I activity during latent infection.

The experimental work is described in detail below. Unexpected results were obtained. No activity of the RNA pol I was detected during latency when a reporter construct was inserted into a HpaI deletion in the LAT region in the opposite orientation to the direction of LAT transcription. However, anti-sense transcripts of the reporter gene sequence were detected in the cytoplasm, showing that the LAT region had been modified for LAP activity to drive during latency expression of transcripts which were exported to the cytoplasm. (Lachmann, Brown and Efstathiou (1996), *J. Gen. Virol.* 77: 2575–2582). An enzyme reporter gene construct inserted into the same site for expression in the correct orientation gave efficient, long-term expression of enzyme activity.

According to a first aspect of the present invention there is provided a nucleic acid construct comprising (i) a portion of the latency associated transcript (LAT) region of a herpes simplex virus (HSV) genome, which portion comprises a latency active promoter (LAP), (ii) an internal ribosomal entry site (IRES) and (iii) a nucleotide sequence heterologous to the herpes virus LAT region.

The heterologous nucleotide sequence may be said to be "operably linked" to the LAP and the IRES for expression of the sequence of amino acids. The term "operably linked" with respect to a nucleotide sequence. (such as a coding sequence) and a promoter means that the nucleotide sequence is positioned or disposed in the nucleic acid construct relative to the promoter suitably for transcription of the nucleotide sequence to be under the control of the promoter. With respect to a nucleotide sequence and an IRES, the term "operably linked" means that the nucleotide sequence is positioned or disposed in the nucleic acid construct relative to the IRES suitably for the IRES to perform its function, i.e. for translation of an mRNA transcript of the sequence to be stimulated or enhanced (i.e. compared with an equivalent construct lacking an IRES operably linked to the nucleotide sequence).

Elements of the LAT promoter important for long term gene expression are not disrupted by insertion-of foreign DNA sequences downstream of the LAT transcription site. Transciption of heterologous sequences in constructs according to the present invention may initiate from the LAT transcription start site, the transcribed RNA being exported to the cytoplasm of latently infected cells.

An IRES is an RNA sequence which facilitates ribosomal attachment and translation from an ATG methionine codon internal to an mRNA. Examples known per se include sequences encoded by picornaviruses. These have been divided into 3 groups; IRES sequences from entero and rhino viruses, from cardio and apthoviruses and from hepatitis A virus. IRES sequences have also been described in other viruses such as hepatitis C and recently in some non-viral organisms.

Mutants, variants and derivatives of naturally occurring IRES sequences may be employed in the present invention provided they retain the ability to enhance translation.

The portion of the LAT comprising a LAP may be subject to mutation or alteration or one or more nucleotides, e.g. by insertion, addition, deletion or substitution to provide a mutant, variant or derivative of a naturally-occurring sequence. Those skilled in the art realise that it is possible to make changes to a nucleic acid molecule which either have no effect on its function or will modulate the level of the activity of interest. Changes which do have an effect may modulate the level of activity in a manner which is useful, e.g. to increase the level of expression or any other desirable property. The present invention must be taken to extend to constructs comprising a mutant, variant or derivative of a LAT sequence, as long as expression is viable in a suitable host cell.

Many known techniques and protocols for manipulation of nucleic acid, for example in preparation of nucleic acid constructs, mutagenesis, sequencing, introduction of DNA into cells and gene expression, and analysis of proteins, are described in detail in *Molecular Cloning: a Laboratory Manual*: 2nd edition, Sambrook et al., 1989, Cold Spring Harbor Laboratory Press and in *Current Protocols in Molecular Biology*, Second Edition, Ausubel et al. eds., John Wiley & Sons, 1992. The disclosures of Sambrook et al. and Ausubel et al. are incorporated herein by reference (as are all references mentioned herein).

The IRES is generally placed downstream of the LAP, while the heterologous nucleotide sequence is placed downstream of the IRES. The heterologous nucleotide sequence and IRES may be placed about 1.5 kb downstream of the transcription start site of the LAT promoter.

The present inventors have found that such a construct may be used to provide efficient, high-level and long-term expression especially where the IRES and coding sequence are inserted downstream of the LAP in place of a HpaI restriction fragment of the LAT region. HpaI cuts after nucleotide 120,301 and before nucleotide 120,469 of the HSV-1 genome. The HSV-1 genome sequence is given in Perry and McGeoch (1988) J. Gen. Virol. 69:2831–2846. Attention is directed to the sequence information provided by Perry and McGeoch, incorporated herein by reference. The boundaries of the LAT promoter are predicted to lie between coordinates 117,010–120,301. They may lie between 118,439–120,301.

Thus, according to a further aspect of the present invention there is provided a nucleic acid construct comprising (i) a portion of the latency associated transcript (LAT) region of a herpes simplex virus (HSV) genome, which portion comprises a latency active promoter (LAP), and (ii) a heterologous nucleotide sequence inserted in the region of a HpaI restriction fragment of the LAT region downstream of the LAP. The heterologous sequence may be inserted in place of the HpaI restriction fragment, or in an adjacent or nearby site. Those skilled in the art can readily determine, by experiments guided by the present disclosure and involving otherwise per se well known procedures, the variation which is possible from the specific insertion described herein without abolishing long-term gene expression.

Where the HSV genomic region employed is derived from HSV-2 rather than HSV-1, the heterologous nucleotide sequence may be inserted at around the same distance from the LAP transcription start site or in the equivalent genomic location in the HSV-2 sequence. The promoter regions of HSV-1 and HSV-2 are very similar. Even though there is some divergence in the sequence of the region in HSV-2 which is equivalent to the HpaI insertion site, the person skilled in the art can readily determine, by experimentation guided by the present disclosure and involving otherwise per se well known procedures, the equivalent position in relation to the LAP of HSV-2 for insertion of a heterolous sequence to give long-term gene expression as disclosed.

The term "heterologous" is used to refer to a nucleotide sequence which is not normally or naturally found in the specified position within the LAT region. It may therefore be any sequence of nucleotides different from the sequence of the fragment found naturally between the two HpaI restriction sites in the LAT region of the herpes simplex virus, i.e. the HpaI restriction fragment. As used in relation to a herpes virus "heterologous" may be used to refer to a non-herpes viral sequence, or a sequence not of the specific herpes virus in question. Possible alternative terminology includes "foreign" or "exogenous".

A heterologous nucleotide sequence may encode a sequence of amino acids, i.e. a peptide or a polypeptide.

Such a nucleotide sequence may be included in constructs of the present invention downstream of an IRES and/or in the region of the HpaI restriction fragment, as discussed. Advantageously, the sequence of amino acids is a protein such as a biologically functional protein whose expression from the construct in cells of an individual has a therapeutic effect.

Alternatively, the nucleotide sequence may on transcription produce a RNA molecule which is able to influence expression of another gene by antisense regulation. The use of anti-sense genes or partial gene sequences to down-regulate gene expression is now well-established. Double-stranded DNA is placed under the control of a promoter in a "reverse orientation" such that transcription of the "antisense" strand of the DNA yields RNA which is complementary to normal mRNA transcribed from the "sense" strand of the target gene. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works.

Another possibility is that the nucleotide sequence on transcription produces a ribozyme, able to cut nucleic acid at a specific site—and thus also useful in influencing gene expression. Background references for ribozymes include Kashani-Sabet and Scanlon, 1995, *Cancer Gene Therapy*, 2(3): 213–223, and Mercola and Cohen, 1995, *Cancer Gene Therapy*, 2(1), 47–59.

In addition to the said heterologous nucleotide sequence, such as a coding sequence, the heterologous nucleotide sequence may comprise one or more regulatory elements to enhance or improve transcription, and/or (for a coding sequence) translation.

In a further aspect, the present invention provides a nucleic acid construct including (a) a herpes viral LAT promoter, (b) located downstream of the promoter, a heterologous nucleotide sequence (polynucleotide), and (c) a further heterologous nucleotide sequence encoding a polyA tail, located downstream of the nucleotide sequence (b). As discussed, a heterologous nucleotide sequence located downstream of the promoter for transcription in the nucleus of a cell containing the construct may encode any desired product, including a polypeptide, an antisense RNA and/or a ribozyme.

In preferred embodiments of various aspects of the present invention the heterologous nucleotide sequence comprises an internal ribosome entry site (IRES) to enhance translation of the coding sequence.

Where a polynucleotide for transcription in a cell nucleus carrying a construct according to the present invention encodes an antisense or ribozyme sequence, there is no need to provide a ribosomal entry site.

Constructs according to the present invention may be used for long-term expression. For instance, expression may be for at least about 26 days, preferably at least about 82 days, more preferably at least about 140 days, at least about 190 days, at least about 257 days, or at least about 307 days. We have observed long-term neuronal gene expression at 257 days post-infection in the peripheral nervous system and up to 9–10 months post infection in the central nervous system, including in the hypoglossal nucleus, facial nerve nucleus and cervical spinal cord. (See Table 1 and discussion in the experimental section below.)

Elements of the LAT promoter important for long term gene expression are not disrupted by insertion of foreign DNA sequences downstream of the LAT transcription site. Transciption of heterologous sequences in constructs according to the present invention may initiate from the LAT transcription start site, the transcribed RNA being exported to the cytoplasm-of latently infected cells.

Embodiments of the invention include the use of viruses such as for example replication defective viruses to obtain long-term gene expression in latently infected cells.

In this connection, the constructs may form part of a vector for introduction into cells. The vector may be a plasmid. A viral vector may be used such as an HSV vector or an HSV-derived vector, e.g. a mutant which is unable to initiate the cycle of productive infection and which may therefore be driven into the latent state or a mutant able to establish latency in cell-types other than neurons. Replication defective and/or attenuated viruses may be preferred for certain purposes.

A replication defective herpes virus may lack a functional form of one or more of the regulatory proteins ICP0, ICP4, ICP22, ICP27 and ICP47, and may lacking additionally or alternatively the essential glycoprotein H (gH) gene, or a functional form thereof. Propagation of a replication defective virus requires a complementing cell line. Cell lines able to complement both ICP4 and ICP27 gene defects have been constructed by Samaniego et al. (*J. Virol.* (1995) 69: 5705–5715). CRI cells are able to supply gH in trans.

A construct according to the present invention may for example be included in a replication defective virus which contains a deletion of the gH gene, and optionally also the ICP4 and ICP27 genes, which virus may be propagated in a suitable complementing host cell.

Thus, according to a further aspect of the invention there is provided a virus or a viral particle comprising as part of its genetic make-up or genome a construct as disclosed. This may be used to introduce the construct into a cell, e.g. a cell of an individual.

Cells comprising a construct according to the present invention are provided as a further aspect of the invention, especially cells in which the construct is incorporated. Such cells may be in culture in vitro, and useful for study of expression etc., or may form part of a mammal, especially a non-human mammal such as a-primate or rodent such as a mouse.

Transgenic animals comprising cells which comprise a construct as disclosed also represent an aspect of the present invention, especially non-human mammals which may be used experimentally to investigate properties of the construct and/or therapeutic potential of delivery of any particular nucleotide sequence to cells of the body, such as neurons.

Methods which comprise introduction of a construct according to the present invention into a cell, e.g. by means of viral infection, are also provided by the invention. This may be performed ex vivo (in vitro) or in vivo. A method according to the present invention may include causing or allowing expression of a heterologous nucleotide sequence in a nucleic acid construct, for instance within a cell following introduction of the construct into the cell or an ancestor thereof. A cell containing a construct according to the invention, e.g. as a result of introduction of the construct into the cell or an ancestor thereof, may be administered to a subject. Following such introduction, cells may be cultured or maintained ex vivo and then delivered to a subject, either from which they were obtained (or from which an ancestor was obtained) or a different subject. Where cells are to be used as an immunogen (for instance), they may be killed or inactivated prior to administration.

Also provided is a method comprising administration of a composition comprising a construct as disclosed to an individual. The administration may be by infection with a viral vector which comprises the construct. Naked DNA delivery may be used.

Stereotactic injection of the therapeutic virus into the nervous system as described by During et al. (ref. 2) is an accepted, efficient and widely used procedure for introducing substances to, or biopsying from, specific regions of the CNS in both humans and animals.

A further method according to an aspect of the present invention includes administration of a herpes virus containing a construct as disclosed.

Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

For intravascular, cutaneous, subcutaneous, intramuscular, intraocular or intracranial injection, or direct injection into cerebrospinal fluid, injection into the biliary tree, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The invention further provides a construct as disclosed, or a vector such as a virus comprising such a construct, for use in a method of treatment of-the human or animal body, and use of such a construct or such a vector in the manufacture of a medicament or composition for use in treatment of the human or animal body. Treatment may be by administration as disclosed above.

Nucleic acid constructs and cells containing them are not just useful in a therapeutic context. It is generally useful to be able to express nucleic acid stably within a host cell in vitro. The results reported herein indicate that stable, long-term expression can be achieved using constructs of the invention. This may therefore be employed in the production of a product encoded by a nucleotide sequence of interest, heterologous to the LAT region of a herpes virus, which may if need be recovered from a host cell for subsequent use. Polypeptides, for instance, are useful in raising antibodies in animals which may be used in the generation of hybridomas for monoclonal antibody production, and selection of antibodies or other binding molecules on columns or by means of bacteriophage display. A polypeptide produced by expression from a heterologous nucleotide sequence included in a construct according to the present invention may of course have a multitude of other uses, depending on the nature of the polypeptide itself.

A cell according to the present invention may be used as an immunogen, for instance, after a period of culture or maintenance ex vivo to allow expression of the heterologous polynucleotide, and optionally after treatment to kill or inactivate the cell.

Numerous other practical applications for constructs, vectors and cells according to the present invention are suggested by the experimental results.

Nervous System Applications
Different Vector Systems

HSV establishes a natural latent state in sensory ganglia neurons that can last the life time of the individual. There is also experimental evidence that defective HSV mutants, which have had certain of the genes required for a productive acute infection deleted, can also establish latency in CNS neurons. Such a vector containing a construct according to the invention should result in long-term expression of these cells as well.

The amplicon vector system consists of a plasmid containing the HSV origin of replication and packaging signals, as well as a promoter reporter gene construct, which can be packaged in a herpes virion for delivery (1). Such vectors produce good reporter gene expression in cells in tissue culture. When used to try to target genes to neurons in animal experiments, however, there has been less success. It has proved very difficult to find promoter constructs that will allow high level gene expression for long periods after infection. Insertion of a construct according to the present invention into an amplicon vector, maintains the LAT region sequences which give rise to long-term gene expression in the native viral genome and should therefore produce long-term, high level expression of an inserted gene.

Similarly, the construct may be inserted into other viral vector systems (i.e. adenovirus, adeno-associated virus or retrovirus systems), or into plasmids used in non-viral delivery systems (e.g. liposomes) to achieve long-term reporter gene expression in the nervous system.

Metabolic Diseases

There are many potential gene therapy applications within the nervous system. One of the main aims is to be able to complement various inborn errors of metabolism which affect the CNS by delivery of a copy of the missing gene. For many such conditions (e.g. Gaucher's Disease) it has been shown that the metabolic defects can be corrected by providing pharmacological amounts of the missing protein. Providing large quantities of such enzymes for pharmacotherapy is often not possible, and, where it is possible, extremely expensive. However, delivery using the present invention of the missing gene directly to the nervous system cells with long-term expression of physiological levels of protein, provides for correction of the metabolic defect with a single treatment. Thus, the present invention may be used for treating a large number of such inherited conditions such as neuronopathic Gaucher's disease and other lysosomal storage disorders, metachromatic leucodystrophy, $G_{M2}$ gangliosidosis, Huntingdon's disease and so on.

There are other neurological diseases due to acquired metabolic abnormalities. In Parkinson's disease there is a loss of cells in the substantia nigra which leads to a deficiency of the neurotransmitter dopamine in the caudate nucleus. Patients can show a good therapeutic response to dopaminergic drugs, but if given orally large doses are needed and the side effects often limit treatment. In this condition it has been shown that providing a local source of the missing chemical in the basal ganglia of the brain can lead to dramatic resolution of symptoms. By delivering the tyrosine hydroxylase gene (which codes the enzyme that makes dopamine) to the cells of the basal ganglia, it is possible. to obtain symptomatic relief in experimental models of the disease (2). Again the present invention provides a way of obtaining long-term gene expression which may be useful for any of these applications. The approach may be usable for a number of other degenerative diseases of the nervous system, such as some of the dementias.

Neoplastic Diseases

Gene therapy also has applications in the treatment of cancer. There are a few rare cancers and neoplastic syndromes that are due to inherited genetic defects (i.e. retinoblastoma, multiple endocrine neoplasia, neurofibromatosis). Some of these may be treated or even prevented by supplying the missing gene by gene therapy. A number of these diseases can affect the cells of the nervous system. Again vector constructs according to the invention may be useful in treatments.

All cancer involves the accumulation of a number of acquired genetic abnormalities which combine to lead to uncontrolled cell division and growth. As we learn more about neoplasia, it is becoming clear that there are a small number of genes which are very important in the aetiology of a large number of cancers. Tumour suppressor genes, such as p53, are good examples of genes which have become inactivated in many neoplastic cell types. Gene therapy may be used to introduce a functional copy of the mutated gene into the neoplastic cells, and hence to arrest their growth. Vectors as disclosed herein may be useful for such applications within the nervous system.

Another approach to gene therapy for cancer is to deliver a suicide gene specifically to the malignant cells which would produce a product which could, directly or indirectly, lead to their death. An example of such a strategy is to use the HSV thymidine kinase (TK) gene containing vectors to specifically transduce malignant cells. The patient is then given acyclovir, which is only metabolised to its active, toxic, metabolite in cells which contain the HSV TK gene. With specific delivery of such a suicide gene to neoplastic cells, constructs of the invention may be used to produce gene expression in neural derived tissue.

Application Outside the Nervous System

Although the LAP is probably most active in neurons, experiments in tissue culture have shown that it can be active in a wide range of other cell types. HSV can infect almost all cell types, though the--only known site of natural latency is in neurons. As noted above, however, it is possible to make defective viruses which are not able to initiate the cycle of productive infection, and such a virus may be driven into the latent state in other cell types.

Then, the LAT region may still be transcriptionally active, though possibly at lower levels than in neurons. The advantage of using an IRES (as discussed) is that is allows very efficient translation of mRNA, and to get appreciable levels of protein product even from a low abundance transcript. This holds for amplicon vectors as well as defective HSV vectors. Thus, HSV vectors containing a gene construct according to the invention may be used for gene delivery to any of a wide range of cell types, e.g. for tackling metabolic and neoplastic diseases, as described above.

Further aspects and embodiments of the present invention will be apparent to those skilled in the art, especially on consideration of the following experimental exemplification which is provided by way of illustration not limitation and with reference to the accompanying figures, wherein:

FIG. 1 shows the plasmid pMENA which contains the murine RNA polymerase 1 promoter, an EMCV IRES and the neomycin resistance gene (ref. 17).

Figure 2:
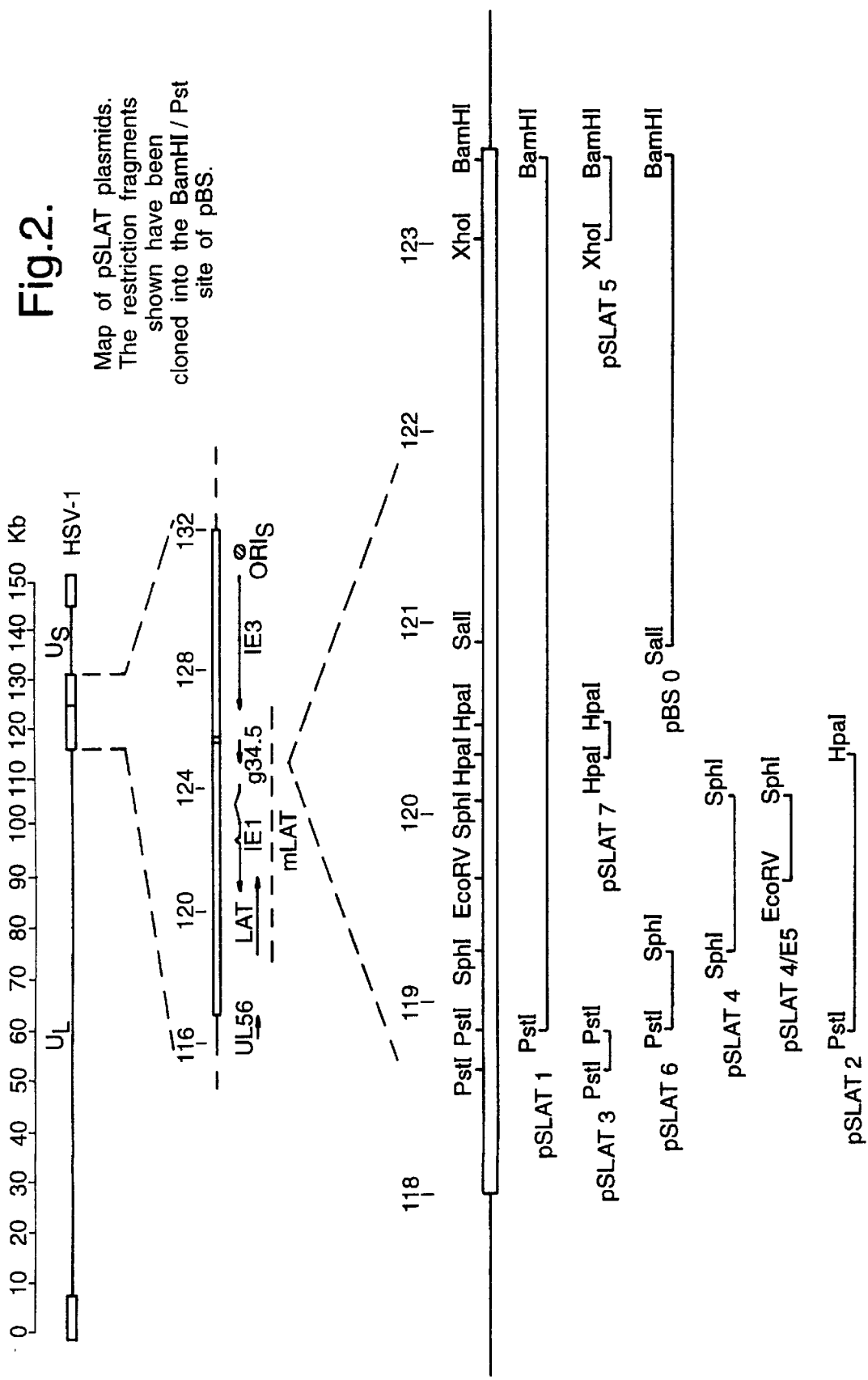

FIG. 2 shows a map of the LAT region encoded by HSV-1. A series of restriction fragments cloned into pbluescribe (Strategene) are shown. These plasmids are designated pSLAT1–pSLAT7. Introduction of foreign DNA sequences into the HSV genome was undertaken by deleting the HpaI fragment (nucleotide position 120,301–120,469 relative to the HSV-1 genomic sequence) of pSLAT1. End repaired foreign DNA was inserted into this locus. Linearized recombinant pSLAT1 was co-transfected with viral DNA and recombinant virus selected from the transfection progeny.

Figure 3:
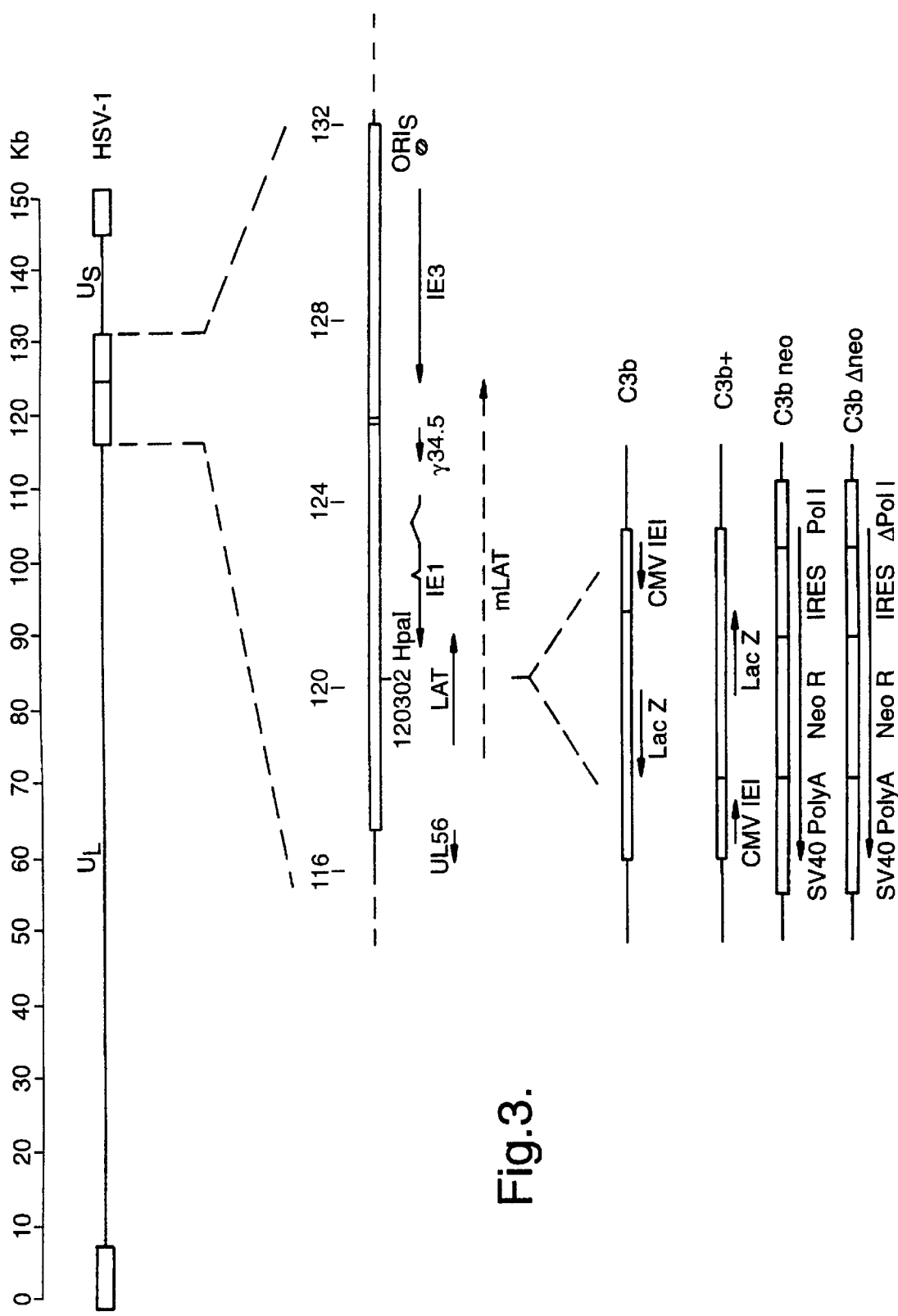

FIG. 3 shows a map to show the structure of viruses C3b, C3b⁺, C3bneo and C3bΔneo.

To make C3b and C3b⁺ a cassette of the CMV IE1 promoter driving β-galactosidase was blunt-end cloned into the HpaI deletion in pSLAT1 (see FIG. 1). Clones containing the insert in each orientation were selected. The recombinant viruses were made by co-transfection of vero cells with PvuI linearised plasmid and HSV strain SC16 DNA. Transfection progeny was screened for β-galactosidase containing viruses, which were plaque purified.

A similar strategy was used to make viruses C3bneo and C3bΔneo. The inserts were prepared from pMENA and pΔMENA (FIG. 2) as XhoI NotI fragments. These were cloned into the HpaI deletion of pSLAT1. Recombinant viruses were made by co-transfecting vero cells with linearised plasmid and C3b viral DNA. Recombinants no longer containing β-galactosidase were plaque purified.

Figure 4:
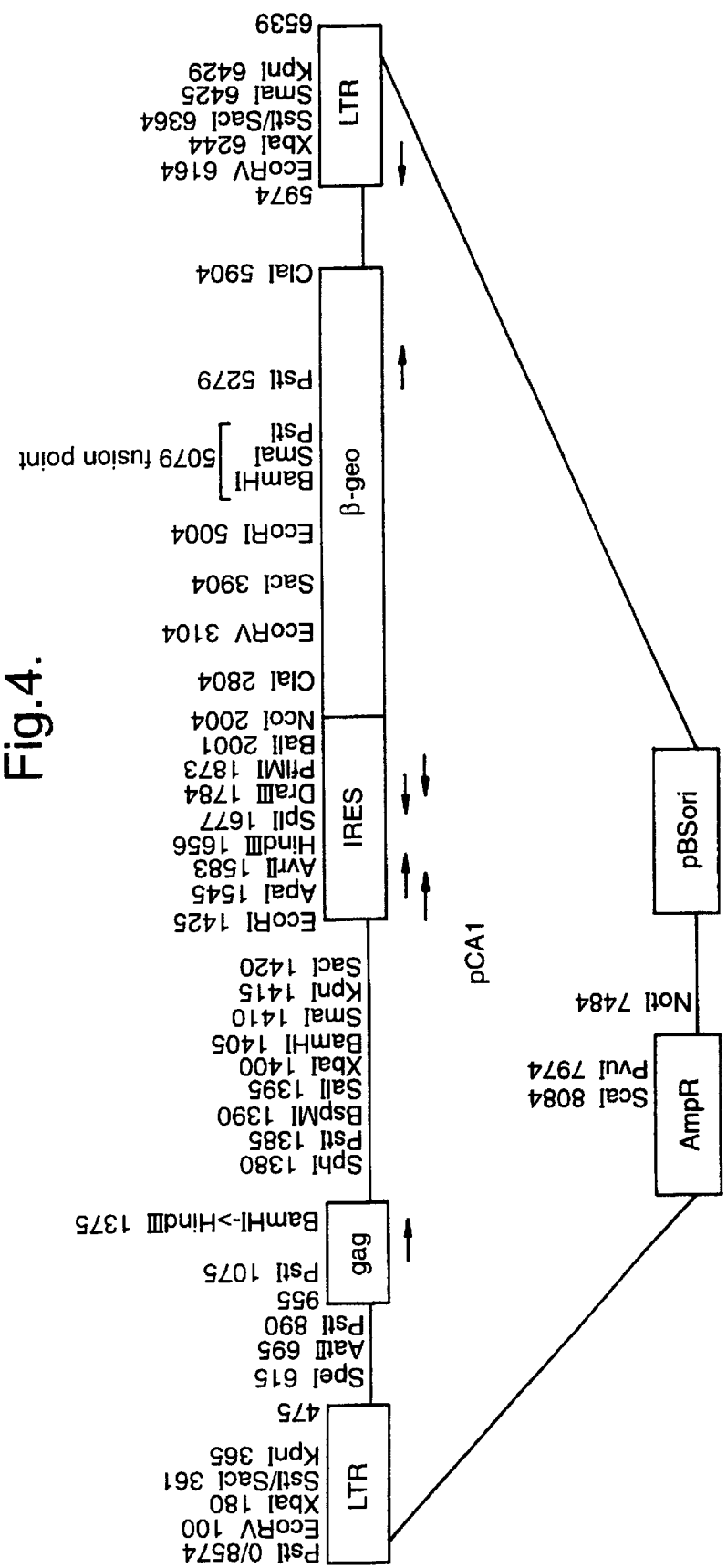

FIG. 4 shows plasmid pCA1.

This plasmid is based on the retroviral vector pBABE (ref: Nucleic Acids Research, 1990, 18, 3587). Into this a cassette containing the encephalomyocarditis virus IRES driving a β-galactosidase neomycin phosphotransferase fusion gene (β-geo) has been cloned. The IRES is derived from the plasmid pEMC2 (Ann Kaminski, Department of Biochemistry, Cambridge).

Figure 5:
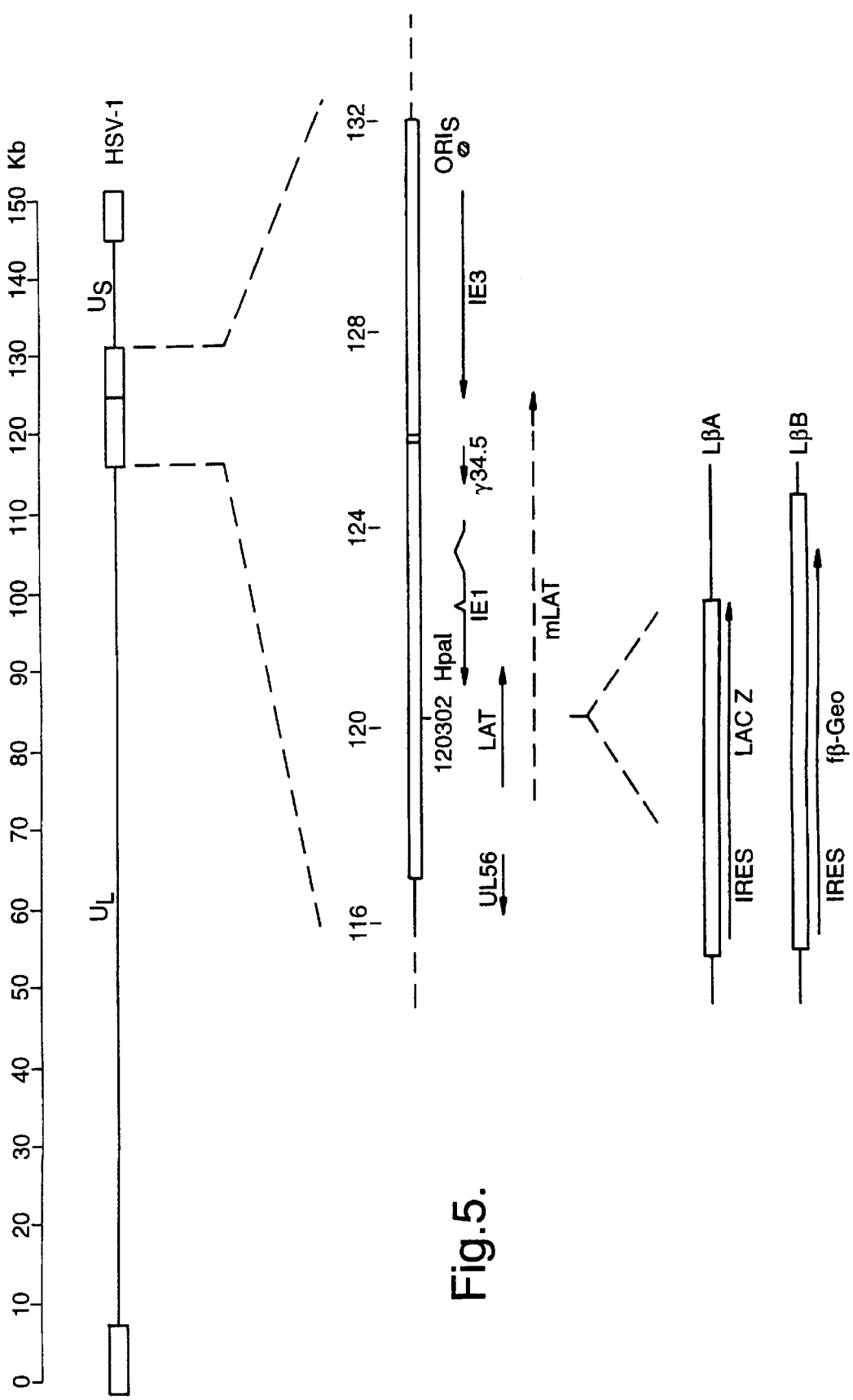

FIG. 5 shows a map to show the structure of viruses LβA and LβB.

These viruses were constructed using the IRES-β-geo insert excised from pCA1 (FIG. 4) as an XbaI fragment. This was cloned into the HpaI deletion of pSLAT1 (FIG. 1). Recombinant virus LβA was made by co-transfection of linearised plasmid with C3b+ viral DNA (FIG. 3). The recombinants express limited β-galactosidase activity in acute infections in vitro, and virus was purified by selecting plaques that did not stain blue with the X-gal reagent. Southern blot analysis of the structure of this virus shows that recombinant occurred within the β-galactosidase-gene, and that no neoR sequences were present.

LβB was made by co-transfection with C3b viral DNA (FIG. 3) and recombinant virus purified as above. This virus contains the complete IRESβgeo sequence.

FIG. 6 shows β-galactosidase expression in PNS from LβA (FIG. 6a) and LβB (FIG. 6b) infected mice. At each time point (days 4, 26, 82, and 190 for LβA and days 5, 32 and 140) for LβB) cervical DRG CII—CIV were dissected from 5 to 6 mice and pooled for histochemical detection of β-galactosidase activity. After staining for 3 hours, the reaction was stopped, and the ganglia clarified in glycerol prior to microscopic examination and enumeration of the number of β-galactosidase expressing neurones.

All documents cited herein are incorporated by reference.

EXAMPLE 1

Vectors Containing RNA Polymerase I Constructs

A series of plasmids containing RNA pol I promoters driving expression of the neomycin resistance gene, with an encephalomyocarditis virus IRES inserted immediately 5' to the reporter gene (the pMENA series of plasmids)-were obtained from Brian McStay (ref. 17) (FIG. 1). The MENA construct was excised as a Xho I Not I fragment, end-repaired and gel purified. This insert was then blunt end cloned into the small Hpa I deletion in pSLAT 1 (FIG. 2), a plasmid designed to allow homologous recombination into the LAT region of HSV-1. Ampicillin resistant colonies were picked, and restriction enzyme analysis confirmed that clones containing the MENA insert in both orientations had been obtained.

In order to avoid confusion with LAP activity, it was decided to insert the MENA construct so that RNA pol I transcription would be in the opposite direction to LAT transcription (FIG. 3). The pSLAT1 clone containing the MENA insert in the correct orientation was prepared by CsCl ultra centrifugation, and linearised by digestion with Pvu I.

Viral DNA was prepared from Vero cells infected at multiplicity of 1 pfu/cell with C3b, and HSV-1 based virus containing the Lac Z gene inserted into the LAT locus (FIG. 3). Cotransfections of Vero cells were done using a $CaCl_2$ precipitation/DMSO shock protocol, and progeny virus was harvested after 3 days, when plaques were beginning to form. Plaque purification was performed under an agarose overlay containing the X-gal substrate, which gives a blue precipitate where β-galactosidase is present, and white plaques were picked. After 3 rounds of plaque purification, viral DNA was prepared, and Southern blot analysis performed to confirm viral structure.

This virus, containing the MENA construct inserted into the LAT region in the anti-sense direction to LAT transcription, is called C3bNeo. A further, similar virus was made using the same method to insert the ΔMENA construct (containing a mutated, inactive RNA pol I promoter) into the LAT region, C3bΔNeo (FIG. 3).

RNA pol I activity from these viruses was initially assessed during acute infection of cells in tissue culture. Monolayers of BHK, Vero and 3T3 cells were infected at high multiplicity, and lysates prepared at various time points for assay of neomycin phosphotransferase activity. The results showed that there is specific RNA pol I activity, most actively in BHK cells, and that the IRES is able to allow efficient translation and production of protein product.

To investigate whether the C3bNeo virus exhibited any RNA pol I activity during latency, 6 week old female Balb/C mice were infected with $2 \times 10^6$ plaque forming units (pfu) of C3bNeo by subcutaneous injection into the left ear (20 μl injection volumes were used). Groups of 10 mice were sacrificed on day 30 and day 180 post infection. Left cervical dorsal root ganglia 2 through 4 were dissected from each mouse, pooled and fixed in periodate lysine paraformaldehyde (PLP) fixative for 1 hour. They were then transferred to 50% ethanol prior to mounting in wax.

5 micron sections were cut and in situ hybridisation performed using digoxigenin labelled riboprobes for both sense and anti-sense (as a control) NeoR transcription. No neomycin phosphotransferase mRNA was detected, indicating that there was no detectable transcription from the RNA pol I promoter in viral latency. Surprisingly, however, we were able to detect transcripts which were being made in the anti-sense direction to the MENA insert. These transcripts were localised to the cytoplasm and occurred at a frequency of 0.8 positive neurons per ganglionic section examined.

It seemed most likely that these transcripts represented LAP activity, and that, by making a large insertion into the LAT region, we had altered LAT processing such that the transcripts were no longer retained in the nucleus, but were exported to the cytoplasm. We confirmed that these cytoplasmic transcripts did contain LAT sequences by further ISH using probes for the 2 kb LAT.

We have also demonstrated cytoplasmic LAT transcripts in latency with the viruses C3b and C3b+ (FIG. 3). This shows that this phenomenon is not specific to the MENA insert, but appears to happen whatever insert is placed into this small Hpa I deletion.

The nuclear LATs seen in wild type HSV latency are unlikely to represent mRNA, as no translation can take place in the nucleus. It has been suggested that they might represent a stable intron which has been excised from a larger mRNA, but conclusive evidence for such a large mRNA has not been found. Our insertion into the LAT region seems to have led to the production of a LAT species which is distributed like a mRNA.

In effect, this is a virus where the LAP drives expression of an mRNA species which can be detected at high levels during latency. From this, on insertion of a reporter gene into this locus or other adjacent loci within major LAT, observation of long-term gene expression was expected. However, there are a number of stop codons between the TATA box of the LAP and the Hpa I deletion used for insertion of coding sequences, and it seemed unlikely that a reporter gene inserted directly into this locus would be expressed.

EXAMPLE 2

Vectors Containing IRES-Reporter gene Constructs in the LAT Region

A plasmid containing an encephalomyocarditis virus IRES linked to a Lac Z/Neo R fusion gene (termed β-Geo)

(pCa1, FIG. 4) was obtained from Clare Abram (Dept of Pathology, Cambridge). The IRES-β-geo insert was cut out as an Xba I fragment, and blunt end cloned into the Hpa I deletion of pSLAT 1. A clone containing the insert in the right orientation, sense to LAT (pSLAT 1 β-Geo), was isolated, and DNA prepared by CsCl ultra centrifugation.

Two viruses have been made using this insertion plasmid. The first was made by co-transfection with viral DNA from C3b+ (FIG. 3). The recombinant was plaque purified and its sequence analysed by Southern blot hybridisation. This showed that a the crossover had occurred during recombination within the Lac Z gene, and that the virus did not contain any Neo R sequences. This virus is called LβA (FIG. 5).

A second virus was made by cotransfection of Vero cells with pSLAT 1 β-Geo and C3b DNA. Again the recombinant virus was plaque purified and its structure confirmed by Southern blot. This virus is called LβB (FIG. 5).

Both these viruses have a shared phenotype in acute infections of Vero cells in tissue culture. If a suspension plaque assay is performed, and staining for β-galactosidase performed, the plaques are predominantly white, but, if examined under the microscope, each plate will contain a few strongly positive blue cells, giving a unique speckled effect. Hence it seems that during acute infection of these non-neuronal cells, the LAP can be active, but only in a proportion of the cells. What constitutes the switch for LAP activity is unclear.

LAP is supposed to show a degree of neuronal specificity, so LAP activity from these viruses was studied during acute and latent infections of mice.

11 female Balb/C mice, aged 5–6 weeks, were infected with $5\times10^6$ pfu of LβA in their left ears, and 5 mice with $5\times10^6$ pfu C3b. 5 mice from each group were sacrificed at day 5 post infection, and the remaining LβA mice were sacrificed at 26 days post infection. The cervical dorsal root ganglia 2–4 on the left were dissected out and these were pooled in the 3 groups. Ganglia were fixed in 2% paraformaldehyde/0.2% glutaraldehyde in PBS on ice for 1 hour. They were then stained for β-galactosidase activity using the X-gal reagent.

Ganglia were whole mounted under cover-slips, and examined under the microscope. In the C3b+ infected mice, 3 of the ganglia were very strongly positive with high level β-galacosidase expression, and it was impossible to count individual neurons. The day 5 LβA infected ganglia showed some positive staining, but this was not nearly as strong as that seen with the virus containing the CMV IE promoter. There were on average 8.4 positive neurons per ganglion. By day 26 after LβA infection, there was continuing β-galactosidase expression, and this was seen at a higher level, and in more neurons, 20.3 per ganglion on average. Hence, activity of the native LAP is greater in latently infected than acutely infected neurons, as would be expected, and efficient expression from the IRES-reporter gene construct persists into latency.

At day 82 post-infection with LβA virus high level β-galactosidase expression was still seen in dorsal root ganglia at an average of 20.5 blue neurones per ganglion examined. Examination at this time of brainstem and spinal cord showed abundant β-galactosidase expression in large numbers of neurones. Furthermore in ganglia and CNS tissue β-gal expression was detected in unidentified non-neuronal cell types—this is a novel finding. Ganglia containing a large number of neurones expressing β-galactosidase were readily detected 190 days post infection.

Data are shown in FIG. 6a and Table 1. No obvious decrease in the average number of β-galactosidase expressing cells was evident throughout the time course of the experiments.

Following enumeration of β-gal positive neurones in whole mounted ganglia sampled at 82 and 190 days post infection, tissues were paraffin embedded and sectioned on a microtome. This allowed an assessment of the number of blue neuronal profiles within ganglionic sections to be made. At 82 days after infection, 261 blue neuronal profiles were detected in a total of 271 ganglionic sections (an average of 0.96 "blue" neuronal profiles per ganglionic section). From these data the conclusion is that there was no obvious decrease in the numbers of neurones expressing β-galactosidase in ganglia removed from mice at between 82 and 190 days post-infection.

β-galactosidase expression in the peripheral nervous system of mice infected with LβB has also been examined. FIG. 6b shows the numbers of "blue" neurones from whole mounted ganglia removed from animals at various times after infection. As observed for LβA, we were able to demonstrate long-term β-galactosidase expression within latently-infected sensory neurones up to 140 days after infection. However, through the course of this experiment it was noted that the numbers of β-galactosidase positive cells per ganglion (Table 1), and the intensity of staining of cells, appeared to be less with this virus than as observed with LβA. Whole mounted ganglia, sampled from LβB infected animals at 140 days after infection, were embedded in paraffin, and sections scored for "blue" neuronal profiles. 59 positive neuronal profiles out of a total of 612 ganglionic sections were observed (an average of 0.1 "blue" neuronal profiles per ganglionic section)—a figure approximately 10-fold lower than that obtained from LβA material sampled and analysed in a similar manner at 82 and 190 days post infection. In order to determine whether these observed differences between LβA and LβB were due to differences in the efficiencies of lacz during latency, in situ hybridisation (ISH) analyses were performed.

Cervical ganglia (CII–CIV) were dissected and pooled from mice latently infected with LβA and LβB at various time points, and processed for ISH. ISH was performed using a digoxigenin labelled riboprobe which was specific for the detection of lacZ mRNA. The data from these experiments are summarised in Table 1. At 82 days post-infection with LβA, 44 lacZ RNA positive neuronal profiles were detected out of 167 ganglionic sections examined (an average of 0.26 lacZ positive neuronal profiles per ganglionic section), and at 190 days post infection, 42 lacZ RNA positive neuronal profiles were detected out of 162 ganglionic sections examined (an average of 0.26 lacZ positive neuronal profiles per ganglionic section). In each case the signal obtained was predominantly cytoplasmic, and the intensity of signal and mean number of lacZ positive neuronal profiles detected per section were similar at both time points. These data indicate the stable, continued transcription of lacZ specific RNA in sensory ganglia latently infected with LβA.

ISH analyses using a LAT specific probe also resulted in the detection of transcripts within the cytoplasm of latently infected neurones, which is in sharp contrast to the characteristic nuclear localisation of LATs observed during latency with wild type viruses. The localisation of LATs and lacZ specific signals in the cytoplasm of neurones supports the view that hybrid transcripts are generated and transported to the cytoplasm of latently infected neurons. Interestingly, ISH detection of lacz specific RNA in ganglia latently-infected with LβB revealed a different pattern of signal than that observed with LβA. Instead of the uniform cytoplasmic lacZ specific signal observed with LβA, animals latently infected with LβB demonstrated a predominantly nuclear, punctate signal, with a cytoplasmic signal observed in only some of the more intensely stained cells. At 140 days post infection with LβB, ISH analyses revealed 23 lacZ positive neuronal positive profiles out of 128 ganglionic sections examined (an average of 0.18 neuronal lacZ positive profiles/ganglionic sections), and at 257 days post infection 102 lacZ positive profiles were observed in 288 ganglionic sections examined (an average of 0.36 lacZ positive neuronal profiles/ganglionic section). It therefore appears that LβB established transcriptionally active latency at an efficiency comparable to that of LβA. However, despite the fact that similar numbers of latently infected neurones harbour transcriptionally active LβA or LβB genomes, fewer neurones latently infected with LβB scored positive for functional β-galactosidase gene expression. The ISH data suggest that this may be a result of the relatively inefficient translocation of lacZ containing transcripts from the nucleus to the cytoplasm of neurones latently infected with LβB rather than failure of LAT promoter mediated transcription.

β-Galactosidase Expression in Neurones of the Central Nervous System From Mice Latently Infected with LβA Using the mouse ear model it has previously been demonstrated that, following the resolution of acute phase infection, animals harbour latent virus DNA in both brainstem and spinal cord tissue, as well as peripheral sensory ganglia (Efstathiou et al. (1986) *J. Virol.* 57: 446–495). It is also well established that, using this model of infection, virus gains access to the brainstem via the facial nerve, which supplies motor fibres to the ear muscles (Hill et al. *Prog. Brain Res.* (1983) 59: 173–184).

We were, therefore, interested to determine whether latently infected animals would contain neurones expressing β-galactosidase at these sites. To date our studies have focused on an examination of brainstems and cervical spinal cords of mice latently infected with recombinant virus LβA, and has involved analysis of: 3 mice sampled at 2–3 months post infection; 2 mice sampled at 4 months post infection; 1 mouse sampled at 6 months post infection; and 11 mice sampled at 9–10 months post infection. As observed previously in our examination of β-galactosidase expression in latently infected sensory ganglia, there was considerable mouse to mouse variation in the level of transcriptionally active latency established. However, the anatomical distribution of β-galactosidase expression was maintained, and β-galactosidase expressing neurones were consistently detected in the cervical spinal cord, and bilaterally within the facial nerve nuclei and hypoglossal nerve nuclei.

β-galactosidase expression was detected most frequently in the facial nerve nuclei (14 out of 17 mice examined), and 'blue' neurones were often observed throughout the nucleus (in up to 13 consecutive 60 μm sections), with some neurones showing tracking of β-galactosidase into the dendritic tree and axon. The wide distribution of latently infected 'blue' neurones within the facial nucleus would be indicative of virus spread within the nucleus during acute infection. β-galactosidase positive neurones were detected in the hypoglossal nuclei in 8 of the 17 animals examined. Latently infected 'blue' neurones were again commonly observed throughout the nucleus (in up to 15 consecutive 60 μm sections). Cervical spinal cord was not obtained from all mice but β-galactosidase expression was observed in both anterior and posterior horn neurones in 6 out of 14 mice examined. We have observed occasional β-galactosidase expressing neurones in the region of the dorsal column sensory nuclei within the posterior caudal medulla of some mice as well as 'blue' axonal profiles traversing this area. These are likely to represent axons projecting from latently infected sensory neurones located in dorsal root ganglia.

The results obtained using embodiments of the present invention are in sharp contrast to most other attempts to obtain long-term gene expression from HSV based vectors, where gene expression has been at its strongest during the acute infection, and then tailed off during establishment of latency.

Examination of brainstem and spinal cord tissues of mice latently infected with LβA revealed β-galactosidase positive neurones in a number of distinct regions of the CNS at time points ranging from 72 to 307 days after infection.

For construction of a long-term expression cassette which can be used in other vector systems, the LAP-IRES β-geo cassette is being cloned into other regions of the virus, and into an amplicon vector. This is by cloning the Not-1 fragment which contains the LAP (from 118,439 to 122,025 bp) and/or a HpaI fragment (nucleotides 117,010 to 120,301) from the Bam HI B fragment of HSV-1 into the NotI site of pcDNA3 (Invitrogen) to generate pcDNA3/LAT. The XbaI fragment of pCA-1 is then cloned downstream of the LAP sequence at a position corresponding to HSV nucleotide 120,301 in pcDNA3/LAT. The LAP-IRES β-geo cassette can now be excised as a NotI fragment and cloned into HSV amplicons or into other viral loci, or used as a plasmid for naked DNA delivery.

REFERENCES

1. Spaete & Frenkel, *Cell* 30, 295–304 (1982).
2. During, et al., *Science* 266, 1399–403 (1994).
3. Feldman, *Seminars in virology* 5, 207–212 (1994).
4. Goins, et al., *J Virol* 68, 2239–52 (1994).
5. Deshmane, et al., *Virology* 196, 868–72 (1993).
6. Nicosia, et al., *J Virol* 67, 7276–83 (1993).
7. Block, et al., *Virology* 192, 618–30 (1993).
8. Dobson, et al., *J Virol* 63, 3844–51 (1989).
9. Margolis, et al., *Virology* 197, 585–92 (1993).
10. Dobson, et al., *Neuron* 5, 353–60 (1990).
11. Lokensgard, et al., *J Virol* 68, 7148–58 (1994).
12. Wolfe, et al., *Nat Genet* 1, 379–84 (1992).
13. Miyanohara, et al., *New Biol* 4, 238–46 (1992).
14. Fink, et al., *Hum Gene There* 3, 11–9 (1992).
15. Weir et al., *PNAS USA* 90, 9140–4 (1993).
16. Andersen, et al., *Hum Gene There* 3, 487–99 (1992).
17. Palmer, et al., *Nucleic Acid Res* 21, 3451–7 (1993).

TABLE 1

Detection of β-galactosidase expression by histochemical staining and by ISH for mRNA in the peripheral nervous system of mice infected with LβA and LβB.

| Virus | Days post infection | Average number of blue neurones per ganglion (range) | ISH positive neuronal profiles per ganglionic section |
|---|---|---|---|
| LβA | 4 | 8.4 (0–55) | ND |
|  | 26 | 17.1 (0–53) | ND |
|  | 82 | 19.8 (0–55) | 0.26 (44/167) |
|  | 190 | 14.7 (0–85) | 0.26 (42/162) |
| LβB | 5 | 2.8 (0–12) | ND |
|  | 32 | 11.7 (0–43) | 0.36 (68/187) |

TABLE 1-continued

Detection of β-galactosidase expression by histochemical staining and by ISH for mRNA in the peripheral nervous system of mice infected with LβA and LβB.

| Virus | Days post infection | Average number of blue neurones per ganglion (range) | ISH positive neuronal profiles per ganglionic section |
|---|---|---|---|
| | 140 | 14.4 (1–32) | 0.18 (23/128) |
| | 257 | ND | 0.36 (102/288) |

What is claimed is:

1. A recombinant replication defective herpes simplex virus comprising a herpes virus latency active promoter (LAP), an internal ribosome entry site (IRES) operably linked to and downstream of the LAP, and a non-herpes virus nucleotide sequence downstream of the IRES, whereby said herpes simplex virus is able to express said non-herpes virus nucleotide sequence.

2. An isolated cell which has been infected by a recombinant herpes virus according to claim 1.

3. A cell according to claim 2, wherein the cell is a nerve cell.

4. The recombinant herpes virus of claim 1, wherein said heterologous nucleotide sequence and said internal ribosome entry site are inserted about 1.5 kb downstream of a transcription start site of the latency active prqmoter (LAP).

5. The recombinant herpes virus of claim 1, wherein said heterologous nucleotide sequence and said internal ribosome entry site are inserted about 700 base pairs downstream of a core latency associated transcript (LAT) promoter, wherein said core LAT promoter comprises a TATA box and a basal transcriptional regulatory sequence.

6. A method for expressing a heterologous nucleic acid sequence in a cell comprising: introducing a virus according to claim 1 into a cell, wherein said introduction results in the cell expressing the nucleic acid.

7. A method according to claim 6, wherein the cell is a nerve cell.

8. A method according to claim 6, wherein the cell is in vivo.

9. A method for expressing a nucleic acid in a subject, which comprises administering to the subject a recombinant herpes virus according to claim 1, thereby expressing the nucleic acid in the subject.

* * * * *

UNITED STATES PATENT AND TRADEMARK OFFICE
CERTIFICATE OF CORRECTION

PATENT NO. : 6,193,980 B1
DATED : February 27, 2001
INVENTOR(S) : Stacey Efstathiou and Robin Henry Lachmann It is certified that error appears in the above-identified patent and that said Letters Patent is hereby corrected as shown below:

Column 9,
Line 32, "possible." should read -- possible --.

Column 18, claim 4,
Line 4, "prqmoter" should read -- promoter --.

Signed and Sealed this

Twenty-sixth Day of February, 2002

Attest:

JAMES E. ROGAN
Attesting Officer  Director of the United States Patent and Trademark Office